US010905159B2

(12) United States Patent
Janardhan et al.

(10) Patent No.: US 10,905,159 B2
(45) Date of Patent: Feb. 2, 2021

(54) ELECTRONIC SMOKING ARTICLE

(71) Applicant: Altria Client Services LLC, Richmond, VA (US)

(72) Inventors: Srinivasan Janardhan, Glen Allen, VA (US); Georgios D. Karles, Richmond, VA (US); Yezdi B. Pithawalla, Midlothian, VA (US); Christopher Simpson, Richmond, VA (US)

(73) Assignee: Altria Client Services LLC, Richmond, VA (US)

( * ) Notice: Subject to any disclaimer, the term of this patent is extended or adjusted under 35 U.S.C. 154(b) by 942 days.

(21) Appl. No.: 14/337,353

(22) Filed: Jul. 22, 2014

(65) Prior Publication Data

US 2015/0027456 A1 Jan. 29, 2015

Related U.S. Application Data

(60) Provisional application No. 61/858,382, filed on Jul. 25, 2013.

(51) Int. Cl.
*A24F 40/40* (2020.01)
*A61M 11/00* (2006.01)
(Continued)

(52) U.S. Cl.
CPC .............. *A24F 40/40* (2020.01); *A24F 40/57* (2020.01); *A61M 11/002* (2014.02); *A61M 11/042* (2014.02); *A61M 15/0021* (2014.02); *A61M 15/06* (2013.01); *A24F 40/48* (2020.01); *A61M 11/008* (2014.02); *A61M 15/002* (2014.02); *A61M 16/202* (2014.02); *A61M 2205/3368* (2013.01); *A61M 2205/3606* (2013.01); *A61M 2205/3653* (2013.01);
(Continued)

(58) Field of Classification Search
None
See application file for complete search history.

(56) References Cited

U.S. PATENT DOCUMENTS

| 4,945,929 A * | 8/1990 | Egilmex | ............... A24F 47/002 |
| | | | 128/200.21 |
| 5,924,417 A | 7/1999 | Braithwaite | |

(Continued)

FOREIGN PATENT DOCUMENTS

| CN | 101277623 | 10/2008 |
| CN | 102106611 A | 6/2011 |

(Continued)

OTHER PUBLICATIONS

International Search Report and Written Opinion for International Application No. PCT/US2014/047690 dated Oct. 2014.
(Continued)

*Primary Examiner* — Joseph S Del Sole
*Assistant Examiner* — Manley L Cummins, IV
(74) *Attorney, Agent, or Firm* — Harness, Dickey & Pierce, P.L.C.

(57) ABSTRACT

An electronic smoking article includes an aerosol generator and a mouth end insert. The mouth end insert includes a mechanical aerosol converter surface having the capacity to improve characteristics of aerosol produced by the aerosol generator, including sensory attributes.

19 Claims, 4 Drawing Sheets

(51) Int. Cl.
  *A61M 15/06* (2006.01)
  *A61M 11/04* (2006.01)
  *A61M 15/00* (2006.01)
  *A24F 40/57* (2020.01)
  *A61M 16/20* (2006.01)
  *A24F 40/48* (2020.01)

(52) U.S. Cl.
  CPC . *A61M 2205/8206* (2013.01); *A61M 2206/14* (2013.01); *A61M 2206/16* (2013.01)

(56) References Cited

U.S. PATENT DOCUMENTS

| | | | | |
|---|---|---|---|---|
| 6,250,301 | B1* | 6/2001 | Pate | A61M 11/041 128/202.21 |
| 7,845,359 | B2 | 12/2010 | Montaser | |
| 8,127,772 | B2 | 3/2012 | Montaser | |
| 8,997,753 | B2* | 4/2015 | Li | H05B 3/42 131/273 |
| 2007/0102013 | A1* | 5/2007 | Adams | A24F 47/008 131/273 |
| 2007/0267032 | A1* | 11/2007 | Shan | A24F 47/002 131/275 |
| 2008/0110454 | A1* | 5/2008 | White | A61M 11/041 128/200.23 |
| 2008/0149118 | A1* | 6/2008 | Oglesby | A61M 11/047 131/194 |
| 2011/0094523 | A1* | 4/2011 | Thorens | A47F 47/008 131/194 |
| 2011/0120455 | A1* | 5/2011 | Murphy | A24F 47/002 128/200.18 |
| 2011/0126831 | A1* | 6/2011 | Fernandez Pernia | A61M 11/041 128/203.27 |
| 2011/0226236 | A1* | 9/2011 | Buchberger | A61M 11/041 128/200.23 |
| 2011/0290268 | A1* | 12/2011 | Schennum | B65D 83/30 131/330 |
| 2012/0230659 | A1* | 9/2012 | Goodman | F22B 1/282 392/395 |
| 2013/0074842 | A1* | 3/2013 | Boucher | A61M 16/16 128/203.16 |
| 2013/0081642 | A1* | 4/2013 | Safari | A24F 47/008 131/329 |
| 2013/0152922 | A1* | 6/2013 | Benassayag | A61M 15/06 128/202.21 |
| 2013/0192615 | A1 | 8/2013 | Tucker et al. | |
| 2013/0192621 | A1 | 8/2013 | Li et al. | |
| 2013/0192623 | A1* | 8/2013 | Tucker | H01C 17/00 131/329 |
| 2013/0263869 | A1* | 10/2013 | Zhu | A24F 47/008 131/329 |
| 2013/0306064 | A1* | 11/2013 | Thorens | A24F 40/40 128/202.21 |
| 2014/0048086 | A1* | 2/2014 | Zhanghua | A24F 47/008 131/329 |
| 2014/0060556 | A1* | 3/2014 | Liu | A24F 47/008 131/329 |

FOREIGN PATENT DOCUMENTS

| | | | |
|---|---|---|---|
| CN | 202407083 U | 9/2012 | |
| CN | 202750708 | 2/2013 | |
| EP | 2460422 A1 | 6/2012 | |
| GB | 2191718 A | 12/1987 | |
| GB | 2412876 A | 10/2005 | |
| WO | WO-98/08436 A1 | 3/1998 | |
| WO | WO-9808436 A1 * | 3/1998 | A61B 5/097 |
| WO | WO-2007042941 A2 | 4/2007 | |
| WO | WO-2009135729 A1 | 11/2009 | |
| WO | WO-2012063600 A1 | 5/2012 | |
| WO | WO-2012129787 A1 | 10/2012 | |
| WO | WO-2013034512 A1 | 3/2013 | |
| WO | WO-2013083638 A1 | 6/2013 | |

OTHER PUBLICATIONS

First Office Action dated Feb. 5, 2018 issued in Chinese Patent Application No. 201480052641.
1st Official Office Notification from the Patent Office in Israel for Israeli Patent Appl. No. 243757 dated Feb. 24, 2019, along with an English language translation.
Chinese Decision on Rejection for corresponding Application No. 201480052641.X dated Apr. 30, 2019, English translation thereof.
European Search Report for Application No. 14747788.9 dated May 11, 2018.
Second Office Action from the Chinese Patent Office for CN201480052641.X dated Nov. 14, 2018, along with an English language translation.
Malaysian Substantive Examination Adverse Report for corresponding Application No. PI2016000138, dated Jun. 26, 2019.

* cited by examiner

ELECTRONIC SMOKING ARTICLE

CROSS-REFERENCE TO RELATED APPLICATION

This application claims priority under 35 U.S.C. § 119(e) to U.S. provisional Application No. 61/858,382, filed on Jul. 25, 2013, the entire content of which is incorporated herein by reference thereto.

WORKING ENVIRONMENT

Electronic smoking articles are operable to deliver liquid from a liquid supply source to a heater. The heater volatilizes a liquid to form an aerosol having droplets therein. The temperature, size of the droplets, and mixing of the aerosol within the electronic smoking article can affect the sensory experience of the smoker.

SUMMARY OF SELECTED FEATURES

An electronic smoking article includes an outer tube extending in a longitudinal direction, a liquid aerosol formulation, a heater operable to heat the liquid aerosol formulation to a temperature sufficient to volatilize the liquid aerosol formulation and form an aerosol, and a mouth end insert. The mouth end insert includes (a) a downstream end wall having at least one diverging outlet passage extending therethrough, (b) a mechanical aerosol converter (MAC) portion upstream of the end wall and including at least one air passage extending therethrough, and (c) an internal cavity arranged between the downstream end wall and the MAC portion. The internal cavity is in fluid communication with the at least one air passage and the at least one diverging outlet passage. The MAC portion is operable to reduce the size of particles in the aerosol and cool the aerosol produced by the electronic smoking article.

A method of improving organoleptic characteristics of an aerosol produced by an electronic smoking article includes producing an aerosol with an aerosolizes of an electronic smoking article and cooling the aerosol by passing the aerosol through a mechanical aerosol converter disposed upstream of a multi-port mouth end insert.

DETAILED DESCRIPTION

A mouth end insert for an electronic smoking article including a mechanical aerosol converter (MAC) insert (or portion) is described herein. As used herein, the term "electronic smoking article" is inclusive of all types of electronic smoking articles, regardless of form, size or shape, including electronic cigarettes, electronic cigars, electronic pipes, electronic hookahs and the like. The liquid aerosol formulation can include nicotine or be nicotine free. Moreover, the liquid aerosol formulation can include tobacco flavors or instead, or in combination include other suitable flavors.

The mouth end insert includes at least one outlet extending through a transversely extending, downstream end wall, a cylindrical tube extending longitudinally from the downstream end, the MAC insert extending transverse to the longitudinal direction and between opposing sides of the cylindrical tube, and an internal cavity between the downstream end wall and the MAC insert. At least one air passage extends through and/or around the MAC insert so as to allow passage of aerosol therethrough. The MAC insert is at least partially contained within the mouth end insert.

During smoking (vaping), liquid aerosol formulation is volatilized by a heater to form an aerosol and flows downstream towards the mouth end insert. The aerosol impacts the MAC insert at the upstream end of the mouth end insert and larger particles and/or droplets are broken apart before entering the mouth end insert via the at least one air passage in the MAC insert. The aerosol then expands into an internal cavity in the mouth end insert where the aerosol swirls and mixes before exiting the mouth end insert via at least one outlet. Because the aerosol strikes the MAC insert and then flows through the at least one air passage, the aerosol loses (transfers) thermal energy to the MAC insert and is cooled before exiting the article. Moreover, the design of the mouth end insert promotes mixing and swirling of the aerosol within the internal cavity prior to delivery to the smoker via the at least one outlet. Thus, the mouth end insert provides unique sensory experiences as compared to electronic smoking articles lacking a mouth end insert having a MAC insert as described herein.

Figure 1:
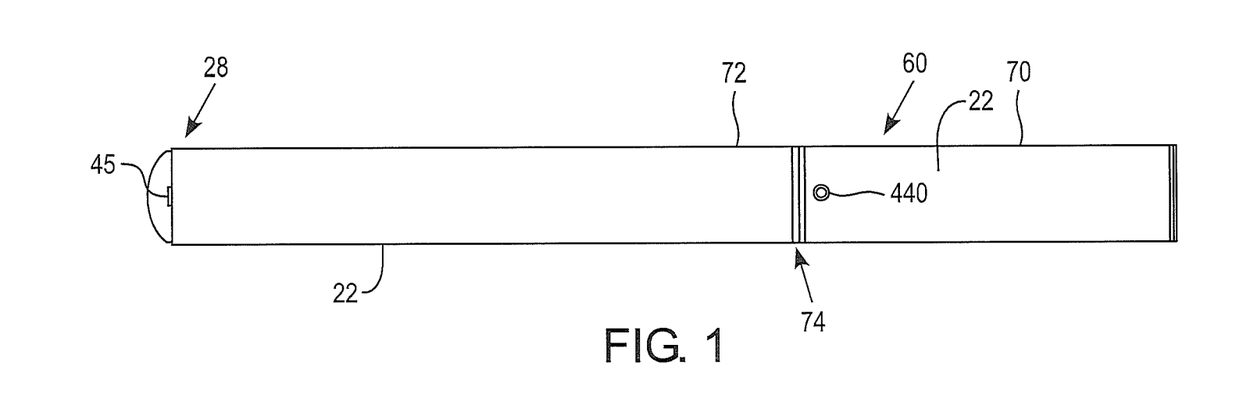
FIG. 1 is an illustration of an electronic smoking article.

The mouth end insert including the MAC insert is used in an electronic smoking article as shown in FIG. 1. The electronic smoking article 60 comprises a replaceable cartridge (or first section) 70 and a reusable fixture (or second section) 72, which are coupled together at a threaded joint 74 or by other convenience such as a snug-fit, snap-fit, detent, clamp and/or clasp.

Figure 3:
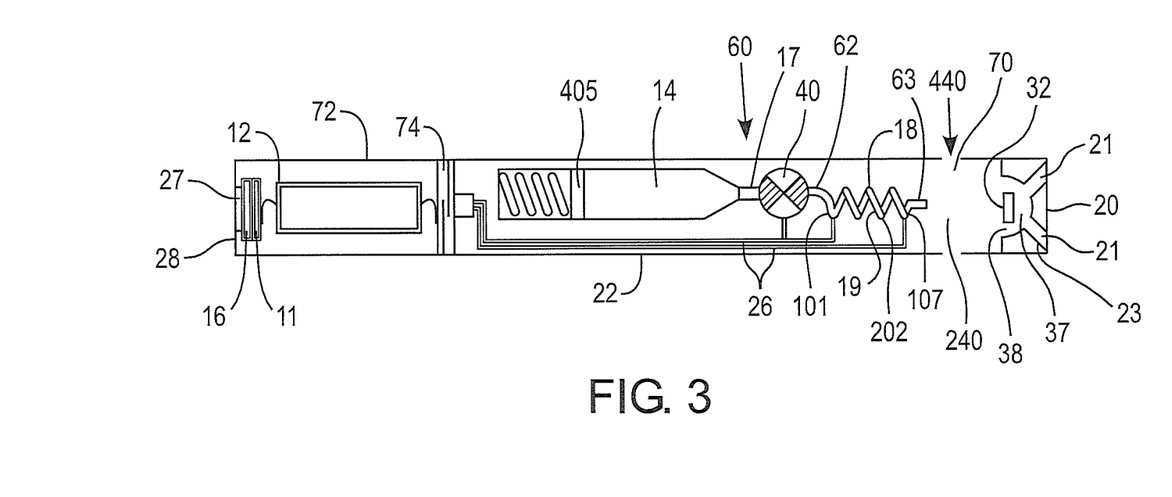
FIG. 3 is a cross-sectional view of a second embodiment of an electronic smoking article.

As shown in FIG. 3, the first section 70 can house a mouth-end insert 20 including a MAC insert 32, a capillary aerosol generator including a capillary (capillary tube) 18, a heater 19 to heat at least a portion of the capillary 18, a liquid supply (reservoir) 14 and optionally a valve 40. Alternatively, as shown in FIG. 4, the first section 70 can house a mouth end insert 20 including a MAC insert 32, a heater 319, a flexible, filamentary wick 328 and a reservoir 314 as discussed in further detail below.

Figure 4:
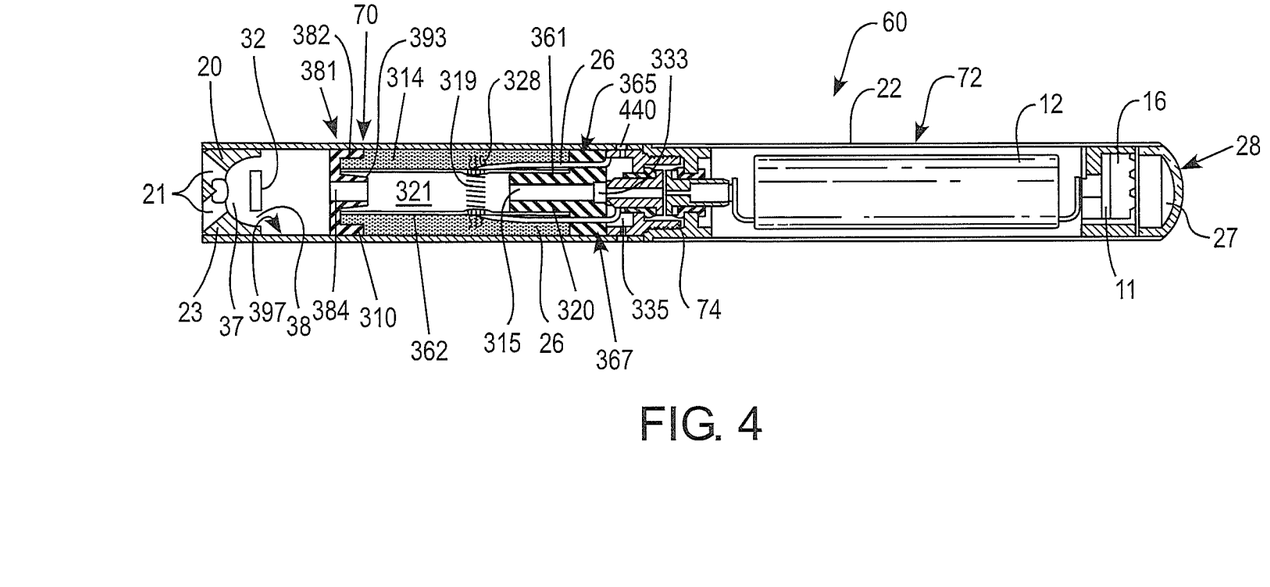
FIG. 4 is a cross-sectional view of a third embodiment of an electronic smoking article.

The second section 72 can house a power supply 12 (shown in FIGS. 2, 3 and 4), control circuitry 11, and optionally a puff sensor 16 (shown in FIGS. 3 and 4). The threaded portion 74 of the second section 72 can be connected to a battery charger when not connected to the first section 70 for use so as to charge the battery.

Figure 2:
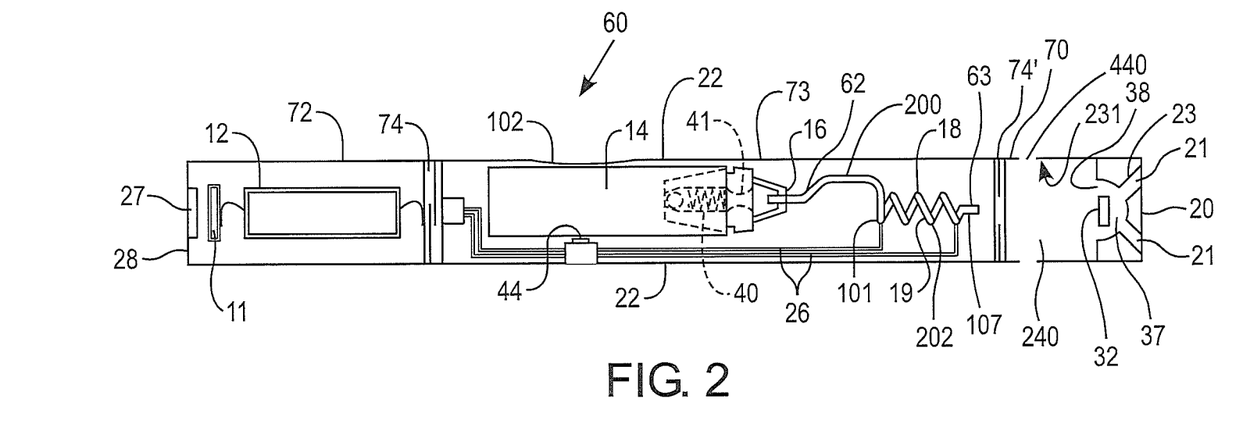
FIG. 2 is a cross-sectional view of a first embodiment of an electronic smoking article.

As shown in FIG. 2, the electronic smoking article 60 can also include a middle section (third section) 73, which can house the reservoir 14, heater 19 and valve 40. The middle section 73 can be adapted to be fitted with a threaded joint 74' at an upstream end of the first section 70 and a threaded joint 74 at a downstream end of the second section 72. In this embodiment, the first section 70 houses the mouth-end insert 20 including the MAC insert 32, while the second section 72 houses the power supply 12 and control circuitry.

Preferably, the first section 70, the second section 72 and the optional third section 73 include an outer cylindrical housing 22 extending in a longitudinal direction along the length of the electronic smoking article 60. Moreover, in one embodiment, the middle section 73 is disposable and the first section 70 and/or second section 72 are reusable. The sections 70, 72, 73 can be attached by threaded connections whereby the middle section 73 can be replaced when the reservoir 14 is depleted.

It is contemplated that the housing 22 may be constructed of a single unitary piece without any threaded connections.

As shown in FIG. 2, the outer cylindrical housing 22 can include a cutout or depression 102 which allows a smoker to manually apply pressure to the reservoir 14. Preferably, the outer cylindrical housing 22 is flexible and/or compressible along the length thereof and fully or partially covers the reservoir 14. The cutout or depression 102 can extend partially about the circumference of the outer cylindrical housing 22. Moreover, the reservoir 14 is compressible such that when pressure is applied to the reservoir, liquid is pumped from the reservoir 14 to the capillary 18. A pressure activated switch 44 can be positioned beneath the reservoir 14. When pressure is applied to the reservoir 14 to pump liquid, the switch is also pressed and a heater 19 is activated. The heater 19 can be a portion of the capillary 18. By applying manual pressure to the pressure switch, the power supply 12 is activated and an electric current heats the liquid in the capillary 18 via electrical contacts so as to volatilize the liquid.

In the preferred embodiment, the reservoir 14 is a tubular, elongate body formed of an elastomeric material so as to be flexible and/or compressible when squeezed. Preferably, the elastomeric material can be selected from the group consisting of silicone, plastic, rubber, latex, and combinations thereof.

Preferably, the compressible reservoir 14 has an outlet 17 which is in fluid communication with a capillary 18 so that when squeezed, the reservoir 14 can deliver a volume of liquid aerosol formulation to the capillary 18. Simultaneous to delivering liquid to the capillary, the power supply 12 is activated upon application of manual pressure to the pressure switch and the capillary 18 is heated to form a heated section wherein the liquid aerosol formulation is volatilized. Upon discharge from the heated capillary 18, the volatilized material expands, mixes with air and forms an aerosol.

Preferably, the reservoir 14 extends longitudinally within the outer cylindrical housing 22 of the first section 70 (shown in FIGS. 3 and 4) or the middle section 73 (shown in FIG. 2). Moreover, the reservoir 14 comprises a liquid aerosol formulation which is volatilized when heated and forms an aerosol when discharged from the capillary 18.

In the embodiments of FIGS. 2 and 3, the capillary 18 includes an inlet end 62 in fluid communication with the outlet 17 of the reservoir 14, and an outlet 63 operable to expel volatilized liquid aerosol formulation from the capillary 18. The reservoir 14 may include a valve 40.

As shown in FIG. 2, the valve 40 can be a check valve that is operable to maintain the liquid aerosol formulation within the reservoir, but opens when the reservoir 14 is squeezed and pressure is applied. Preferably, the check valve 40 opens when a critical, minimum pressure is reached so as to avoid inadvertent dispensing of liquid aerosol formulation from the reservoir 14 or activating the heater 19. Preferably, the critical pressure needed to open the check valve 40 is essentially equal to or slightly less than the pressure required to press a pressure switch 44 to activate the heater 19. Preferably, the pressure required to press the pressure switch 44 is high enough such that accidental heating is avoided. Such arrangement avoids activation of the heater 19 in the absence of liquid being pumped through the capillary.

Advantageously, the use of a check valve 40 aids in limiting the amount of liquid that is drawn back from the capillary upon release of pressure upon the reservoir 14 (and/or the switch 44) if manually pumped so as to avoid air uptake into the reservoir 14. Presence of air degrades pumping performance of the reservoir 14.

Once pressure upon the reservoir 14 is relieved, the valve 40 closes. The heated capillary 18 discharges liquid remaining downstream of the valve 40.

Optionally, a critical flow orifice 41 is located downstream of the check valve 40 to establish a maximum flow rate of liquid to the capillary 18.

As shown in FIG. 3, in other embodiments, the valve 40 can be a two-way valve and the reservoir 14 can be pressurized. For example, the reservoir 14 can be pressurized using a pressurization arrangement 405 which applies constant pressure to the reservoir 14. For example, pressure can be applied to the reservoir 14 using an internal or external spring and plate arrangement which constantly applies pressure to the reservoir 14. Alternatively, the reservoir 14 can be compressible and positioned between two plates that are connected by springs or the reservoir 14 could be compressible and positioned between the outer housing and a plate that are connected by a spring so that the plate applies pressure to the reservoir 14.

Preferably, the capillary 18 of FIGS. 2 and 3 has an internal diameter of 0.01 to 10 mm, preferably 0.05 to 1 mm, and more preferably 0.05 to 0.4 mm Capillaries of smaller diameter provide more efficient heat transfer to the fluid because, with the shorter distance to the center of the fluid, less energy and time is required to vaporize and/or volatilize the liquid aerosol formulation.

Also preferably, the capillary 18 may have a length of about 5 mm to about 72 mm, more preferably about 10 mm to about 60 mm or about 20 mm to about 50 mm. In one embodiment, the capillary 18 is substantially straight. In other embodiments, the capillary 18 is coiled and/or includes one or more bends therein to conserve space and/or accommodate a long capillary.

In these embodiments, the capillary 18 is formed of a conductive material, and thus acts as its own heater 19 by passing current through the capillary. The capillary 18 may be any electrically conductive material capable of being resistively heated, while retaining the necessary structural integrity at the operating temperatures experienced by the capillary 18, and which is non-reactive with the liquid aerosol formulation. Suitable materials for forming the capillary 18 are selected from the group consisting of stainless steel, copper, copper alloys, porous ceramic materials coated with film resistive material, Inconel® available from Special Metals Corporation, which is a nickel-chromium alloy, nichrome, which is also a nickel-chromium alloy, and combinations thereof.

In one embodiment, the capillary 18 is a stainless steel capillary 18, which serves as a heater 19 via electrical leads 26 attached thereto for passage of direct or alternating current along a length of the capillary 18. Thus, the stainless steel capillary 18 is heated by resistance heating. The stainless steel capillary 18 is preferably circular in cross section and may be formed of tubing suitable for use as a hypodermic needle of various gauges. For example, the capillary 18 may comprise a 32 gauge needle has an internal diameter of 0.11 mm and a 26 gauge needle has an internal diameter of 0.26 mm.

In another embodiment, the capillary 18 may be a non-metallic tube such as, for example, a glass tube. In an embodiment, the heater 19 is operative along at least a portion of the glass tube and is formed of a conductive material capable of being resistively heated, such as, for example, stainless steel, nichrome or platinum wire, arranged along the glass tube. When the heater is heated, liquid aerosol formulation in the capillary 18 is heated to a temperature sufficient to at least partially volatilize liquid aerosol formulation in the capillary 18.

Preferably, at least two electrical leads 26 are bonded to a metallic capillary 18. In the preferred embodiment, the at least two electrical leads 26 are brazed to the capillary 18. Preferably, one electrical lead 26 is brazed to a first, upstream portion 101 of the capillary 18 and a second electrical lead 26 is brazed to a downstream, end portion 107 of the capillary 18, as shown in FIGS. 2 and 3.

In use, once the capillary 18 of FIGS. 2 and 3 is heated, the liquid aerosol formulation contained within a heated portion of the capillary 18 is volatilized and ejected out of the outlet 63 where it expands and mixes with air and forms an aerosol in a mixing chamber 240.

As noted above, the liquid aerosol formulation can also be used in an electronic smoking article including a heater 319 and a filamentary wick 328 as shown in FIG. 4. The first section 70 includes an outer tube (or casing) 22 extending in a longitudinal direction and an inner tube (or chimney) 362 coaxially positioned within the outer tube 22. Preferably, a nose portion 361 of an upstream gasket (or seal) 320 is fitted into an upstream end portion 365 of the inner tube 362, while at the same time, an outer perimeter 367 of the gasket 320 provides a liquid-tight seal with an interior surface 397 of the outer casing 22. The upstream gasket 320 also includes a central, longitudinal air passage 315, which opens into an interior of the inner tube 362 that defines a central channel 321. A transverse channel 333 at an upstream portion of the gasket 320 intersects and communicates with the central, longitudinal air passage 315 of the gasket 320. This channel 333 assures communication between the central, longitudinal air passage 315 and a space 335 defined between the gasket 320 and a threaded connection 74.

Preferably, a nose portion 393 of a downstream gasket 310 is fitted into a downstream end portion 381 of the inner tube 362. An outer perimeter 382 of the gasket 310 provides a substantially liquid-tight seal with an interior surface 397 of the outer casing 22. The downstream gasket 310 includes a central channel 384 disposed between the central passage 321 of the inner tube 362 and the mouth end insert 20.

In this embodiment, the reservoir 314 is contained in an annulus between an inner tube 362 and an outer casing 22 and between the upstream gasket 320 and the downstream gasket 310. Thus, the reservoir 314 at least partially surrounds the central air passage 321. The reservoir 314 comprises a liquid aerosol formulation and optionally a liquid storage medium (not shown) operable to store the liquid aerosol formulation therein.

The inner tube 362 has a central air passage 321 extending therethrough which houses the heater 319. The heater 319 is in contact with the filamentary wick 328, which preferably extends between opposing sections of the reservoir 314 so as to deliver the liquid aerosol formulation from the reservoir to the heater 319.

Preferably, the electronic smoking article 60 of each embodiment described herein also includes at least one air inlet 440. As shown in FIG. 4, the at least one air inlet 440 can be located upstream of the heater 319.

In the embodiments of FIGS. 2 and 3, the at least one air inlet 440 is arranged downstream of the capillary 18 so as to minimize drawing air along the capillary and thereby avoid cooling of the capillary 18 during heating cycles.

The at least one air inlet 440 includes one or two air inlets. Alternatively, there may be three, four, five or more air inlets. Altering the size and number of air inlets 440 can also aid in establishing the resistance to draw of the electronic smoking article 60.

The power supply 12 of each embodiment can include a battery arranged in the electronic smoking article 60. The power supply 12 is operable to apply voltage across the heater 19 associated with the capillary 18, as shown in FIGS. 2 and 3, or the heater 319 associated with the filamentary wick 328, in the embodiments of FIG. 4. Thus, the heater 19, 319 volatilizes liquid aerosol formulation according to a power cycle of either a predetermined time period, such as a 2 to 10 second period.

Preferably, the electrical contacts or connection between the heater 19, 319 and the electrical leads 26 are highly conductive and temperature resistant while the heater 19, 319 is highly resistive so that heat generation occurs primarily along the heater 19, 319 and not at the contacts.

The battery can be a Lithium-ion battery or one of its variants, for example a Lithium-ion polymer battery. Alternatively, the battery may be a Nickel-metal hydride battery, a Nickel cadmium battery, a Lithium-manganese battery, a Lithium-cobalt battery or a fuel cell. In that case, preferably, the electronic smoking article 60 is usable by a smoker until the energy in the power supply is depleted. Alternatively, the power supply 12 may be rechargeable and include circuitry allowing the battery to be chargeable by an external charging device. In that case, preferably the circuitry, when charged, provides power for a pre-determined number of puffs, after which the circuitry must be re-connected to an external charging device.

Preferably, the electronic smoking article 60 of each embodiment also includes control circuitry which can be on a printed circuit board 11 (shown in FIGS. 2, 3 and 4). The control circuitry 11 can also include a heater activation light 27 that is operable to glow when the heater 19, 319 is activated. Preferably, the heater activation light 27 comprises at least one LED and is at an upstream end 28 (shown in FIGS. 1 and 3) of the electronic smoking article 60 so that the heater activation light 27 illuminates a cap which takes on the appearance of a burning coal during a puff. Moreover, the heater activation light 27 can be arranged to be visible to the smoker. In addition, the heater activation light 27 can be utilized for aerosol generation article system diagnostics. The light 27 can also be configured such that the smoker can activate and/or deactivate the light 27 when desired, such that the light 27 would not activate during smoking if desired.

The time-period of the electric current supply to the heater 19 may be pre-set depending on the amount of liquid desired to be vaporized. The control circuitry 11 can be programmable and can include an application specific integrated circuit (ASIC). In other embodiments, the control circuitry 11 can include a microprocessor programmed to carry out functions such as heating the capillaries and/or operating the valves.

In a preferred embodiment, the electronic smoking article 60 is about the same size as a conventional smoking article. In some embodiments, the electronic smoking article 60 can be about 80 mm to about 110 mm long, preferably about 80 mm to about 100 mm long and about 7 mm to about 8 mm in diameter. For example, in an embodiment, the electronic smoking article is about 84 mm long and has a diameter of about 7.8 mm.

The outer cylindrical housing 22 of the electronic smoking article 60 may be formed of any suitable material or combination of materials. Preferably, the outer cylindrical housing 22 is formed at least partially of metal and is part of the electrical circuit.

The housing 22 is preferably circular in cross-section, but may instead by rectangular, square, oval, triangular or any other form in cross-section.

In the embodiment shown in FIG. 2, at least a portion of the outer cylindrical housing 22 can be elastomeric so as to allow a smoker to squeeze the housing 22 and the reservoir 14 during smoking to release liquid aerosol formulation therefrom and activate the heater 19. Thus, the outer cylindrical housing 22 can be formed of a variety of materials including plastics, rubber and combinations thereof. In a preferred embodiment, the outer cylindrical housing 22 is formed of silicone. The outer cylindrical housing 22 can be any suitable color and/or can include graphics or other indicia printed thereon.

Preferably, the reservoir 14, 314 contains a liquid aerosol formulation, which includes at least one aerosol former, optionally water, a nicotine source, and at least one flavorant.

In the embodiments, the at least one aerosol former is selected from the group consisting of propylene glycol, glycerin and combinations thereof. Preferably, the at least one aerosol former is included in an amount ranging from about 40% by weight based on the weight of the liquid formulation to about 90% by weight based on the weight of the liquid formulation (e.g., about 50% to about 80%, about 55% to about 75% or about 60% to about 70%). Moreover, in one embodiment, the liquid formulation can include propylene glycol and glycerin included in a ratio of about 3:2.

Preferably, the liquid formulation also includes water. Water can be included in an amount ranging from about 5% by weight based on the weight of the liquid formulation to about 40% by weight based on the weight of the liquid formulation, more preferably in an amount ranging from about 10% by weight based on the weight of the liquid formulation to about 15% by weight based on the weight of the liquid formulation.

The liquid aerosol formulation optionally includes at least one flavorant in an amount up to about 15% by weight (e.g., about 0.1% to about 15%, about 1% to about 12%, about 2% to about 10%, or about 5% to about 8%). The at least one flavorant can be a natural flavorant or an artificial flavorant. Preferably, the at least one flavorant is selected from the group consisting of tobacco flavor, menthol, wintergreen, peppermint, herb flavors, fruit flavors, nut flavors, liquor flavors, and combinations thereof.

Preferably, the liquid aerosol formulation also includes at least one nicotine source. The nicotine is included in the liquid aerosol formulation in an amount up to about 10% by weight (e.g., about 1% to about 10%, about 2% to about 9%, about 2% to about 8%, about 2% to about 6%).

As shown in FIGS. 2, 3, 4, 5, 6, 7, 8, 9, 10 and 11, the electronic smoking article 60 further includes the mouth end insert 20, which comprises a transverse end wall 30 having at least one outlet passage 21, a mechanical aerosol converter (MAC) insert (portion) 32, and a cavity 37 disposed between the end wall 30 and the MAC insert 32. The mouth end insert 20 preferably includes multiple outlets 21 extending through the transverse downstream end wall 30 and an outer cylindrical surface 29 extending longitudinally from the downstream end wall 30, which is sized to fit into an end portion of an electronic smoking article 60. Preferably, the MAC insert 32 is disposed centrally across a portion of the internal cavity 37. The MAC insert 32 includes at least one air passage 38 so as to allow passage of aerosol therethrough. In these embodiments, the MAC insert 32 is at least partially contained within the internal cavity 37 of the mouth end insert 20. Preferably, the downstream end wall 30 is generally planar and has at least one off-axis, diverging outlet 21 (e.g., at least two) extending therethrough, more preferably, four.

Also preferably, the internal cavity 37, shown in FIGS. 2, 3 and 4, is arranged between the MAC insert 32 and the downstream end wall 30 of the mouth end insert 20. Preferably, the internal cavity is about 1.0 mm to about 5.0 mm in length and is domed in form although the internal cavity 37 may be cylindrical instead. Preferably, the diameter of the internal cavity ranges from about 0.25 mm to about 1.25 mm (e.g., about 0.50 mm to about 1.0 mm or about 0.75 mm to about 0.95 mm) The internal cavity 37 is sized and configured to allow aerosol to mix and swirl therein after passing through the at least one air passage 38.

The MAC insert 32 may comprise a disc 332 (such as in the embodiment of FIG. 8) or a bar 432 (such as in the embodiment of FIG. 9). having a thickness ranging from about 0.25 min to about 1.25 mm (e.g., about 0.50 mm to about 1.0 mm or about 0.75 min to about 0.95 mm). The peripheries of the MAC insert 32 disc or bar can be sized and configured to friction fit within interior surfaces of an end portion 290 of the mouth end insert 20. Optionally, an annular groove may be provided in the cylindrical end portion 290 to retain the disc 332 and/or the bar 432.

Preferably, the mouth end insert 20 includes at least one diverging outlet 21 (e.g., 2, 3, 4, 5, or preferably 6 to 8 outlets or more). Preferably, the outlets 21 of the mouth end insert 20 are located at ends of off-axis passages 23 and are angled outwardly in relation to the longitudinal direction of the electronic smoking article 60 (i.e., divergently). As used herein, the term "off-axis" denotes at an angle to the longitudinal direction of the electronic smoking article. Also preferably, the mouth end insert (or flow guide) 20 includes outlets uniformly distributed around the mouth end insert 20 so as to substantially uniformly distribute aerosol in a smoker's mouth during use. As the aerosol passes into a smoker's mouth, the aerosol enters the mouth and moves in different directions so as to provide a full mouth feel as compared to electronic smoking article s having an on-axis single orifice which directs the aerosol toward a single location in a smoker's mouth.

In the preferred embodiment, the outlets 21 of the mouth end insert 20 are located at the ends of the off-axis passages 23 and are angled at 5 to 60° with respect to the central longitudinal axis of the electronic smoking article 60 so as to more completely distribute aerosol throughout a mouth of a smoker during use and to remove droplets.

Preferably, each outlet 21 has a diameter of about 0.015 inch to about 0.090 inch (e.g., about 0.020 inch to about 0.040 inch or about 0.028 inch to about 0.038 inch). The size of the outlets 21 and off-axis passages 23 along with the number of outlets 21 can be selected to adjust the resistance to draw (RTD) of the electronic smoking article 60, if desired.

Figures 5, 6, 7, 8, 9, 10:
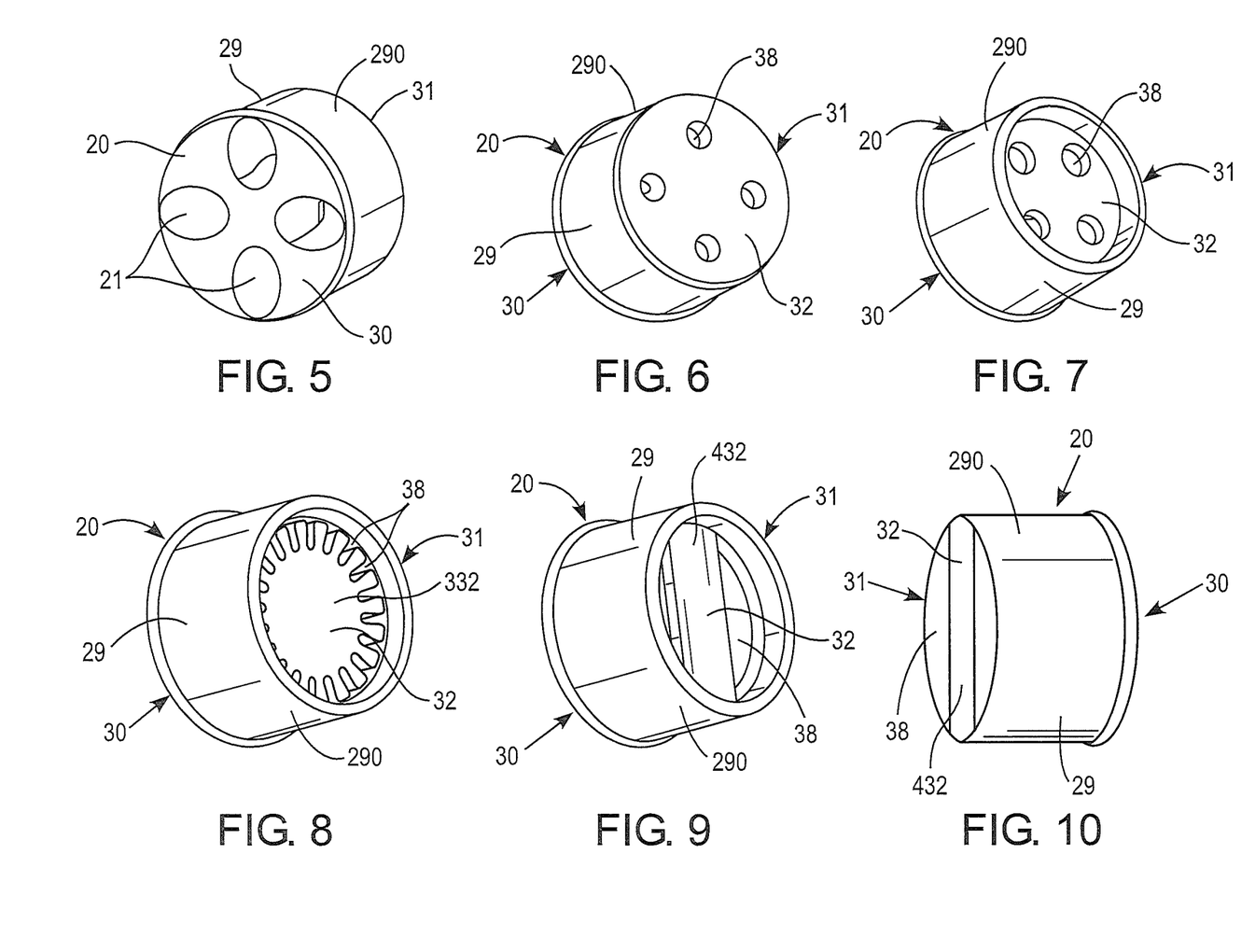
FIG. 5 is a perspective view of a downstream end wall of a mouth end insert as described herein.
FIG. 6 is a perspective view of an upstream end of a first embodiment of a mouth end insert as described herein.
FIG. 7 is a perspective view of an upstream face of a second embodiment of a mouth end insert as described herein.
FIG. 8 is a perspective view of an upstream face of a third embodiment of a mouth end insert as described herein.
FIG. 9 is a perspective view of an upstream face of a fourth embodiment of a mouth end insert as described herein.
FIG. 10 is a perspective view of an upstream face of a fifth embodiment of a mouth end insert as described herein.

Referring now to FIG. 6, in one embodiment, the MAC insert 32 is substantially disc-shaped and includes at least one air passage 38, preferably four air passages 38, substantially uniformly arranged about an outer periphery portion of the MAC insert 32. The MAC insert 32 can include 4 to 25 air passages 38 extending therethrough. Preferably, a central portion of the MAC insert 32 is air impermeable such that aerosol impacts the central portion of the MAC insert 32 prior to passing through the air passages 38. Preferably, each of the air passages 38 has a diameter ranging from about 0.25 mm to about 1.25 mm (e.g., about 0.50 mm to about 1.0 mm or about 0.75 mm to about 0.95 mm).

In some embodiments, the air passages 38 are sized so as not to impact the desired resistance to draw (RTD) of the electronic smoking article 60. Optionally, the size and number of the air passages 38 is chosen to establish the RTD of the electronic smoking article 60. In such case, the at least one air passage 38 is preferably sized to provide an RTD of about 80 to about 140 mm of $H_2O$ (e.g., about 90 to about 130 mm of $H_2O$ or about 100 to about 120 mm of $H_2O$). Moreover, the MAC insert 37 can be flush with the plane defined by an upstream edge of the cylindrical portion 290. However, as shown in FIG. 7, the MAC insert 37 can be recessed within the cylindrical portion 290 so as to reduce the size of the internal cavity 37 (shown in FIGS. 2, 3 and 4).

During use, aerosol initially strikes the MAC insert 32 and droplets and particles within the aerosol are broken up and reduced in size. In addition, contact with the MAC insert 32 results in thermal energy transfer and cooling of the aerosol.

Figure 12:
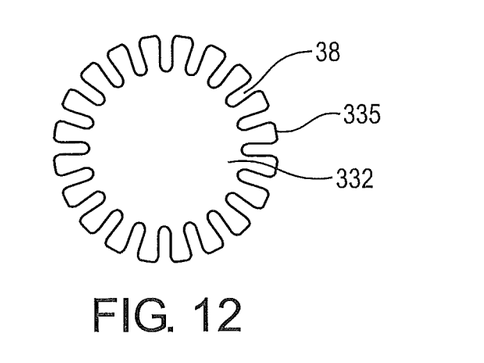
FIG. 12 is a detailed planar view of the MAC insert of the embodiment of FIG. 8.

As shown in FIGS. 8 and 12, the MAC insert 32 can include a plurality of air passages 38 (e.g., 10 to 40, preferably 15 to 30, more preferably about 25) spaced at an outer periphery of the MAC insert 32, such that the MAC insert 32 is substantially gear-shaped and the air passages 38 extend between the MAC insert 32 and an inner surface of the cylindrical portion 290 of the mouth end insert 20. Preferably, each of the air passages 38 is substantially square, trapezoidal, or rectangular in shape and has a width and a length ranging from about 0.15 mm to about 1.0 mm (e.g., about 0.20 mm to about 0.90 mm, about 0.30 mm to about 0.80 mm, about 0.40 mm to about 0.70 mm or about 0.50 mm to about 0.60 mm). Optionally, the dimensions of the air passages 38 can be chosen to provide a predetermined RTD as described in reference to FIGS. 6 and 7. The MAC insert 32 of FIGS. 8 and 12 can be manufactured using wire electric discharge machining (EDM). The MAC insert 32 of FIG. 12 illustrates a gear shaped insert modified for manufacturability by stamping.

During use, aerosol initially strikes the MAC insert 32 and the aerosol flow is split into several parts as it is channeled through the plurality of air passages 38. As the aerosol strikes the MAC insert 32, the MAC insert 32 acts as a heat sink and the aerosol is cooled upon impact. Moreover, the droplets and particles within the aerosol are broken up and reduced in size before flowing through the plurality of air passages 38. Additional heat transfer (and cooling) occurs as the aerosol passes through the air passages 38 of the MAC insert 32. The embodiment of FIG. 8 is believed to enhance such further cooling with its comparatively small air passages 38. Contact with the MAC insert 32 results in thermal energy transfer.

In yet another embodiment, as shown in FIGS. 9 and 10, the MAC insert 32 can comprise one or more bars 432 extending between opposing portions of the cylindrical portion 290. Each bar-shaped MAC insert 32 can friction fit between opposing sides of the cylindrical portion 290. Moreover, the MAC insert 32 can include at least one air passage 38 extending along and/or around each bar-shaped MAC insert 32. In the preferred embodiment, each bar has a width ranging from about 1 mm to about 4 mm (e.g., about 1.5 mm to about 2.5 mm or about 2 mm to about 3 mm). Preferably, the aerosol strikes the one or more bars and then flows through the air passages 38 on either side of the one or more bars and into the internal cavity 37.

As shown in FIG. 9, the bar shaped MAC insert 32 can be recessed within the cylindrical tube 29. Alternatively, as shown in FIG. 10, the bar shaped MAC insert 32 can be flush with the upstream end 31 of the cylindrical tube 29.

Figure 11:
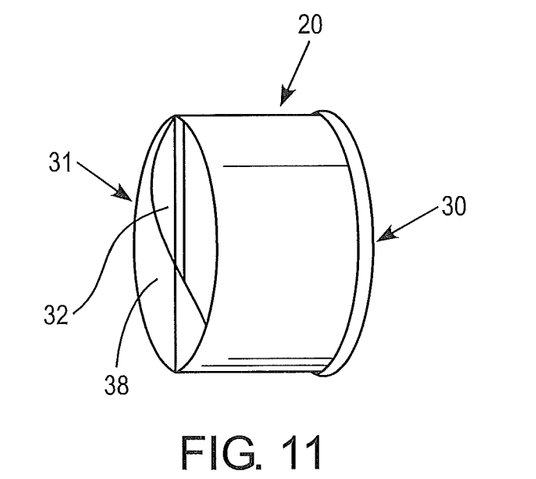
FIG. 11 is a perspective view of an upstream face of a sixth embodiment of a mouth end insert as described herein.

In another embodiment, shown in FIG. 11, the MAC insert 32 of the mouth end insert 20 can be in the form of one or more vanes, upon which the aerosol impacts before entering the internal cavity 37. Preferably, the vanes are substantially spiral shaped. In the preferred embodiment, each vane has a width ranging from about 0.1 mm to about 6 mm (e.g., about 0.5 mm to about 5 mm, about 1 mm to about 4 mm or about 2 mm to about 3 mm).

Preferably, the MAC insert 32 of the mouth end insert 20 is disposed a predetermined spacing from the downstream gasket 310 or the capillary 18. In a preferred embodiment, that distance is in the range of about 1 mm to about 3 mm, more preferably in the range of about 1.5 mm to about 2.5 mm, but could be set at other values based on testing and/or modeling data.

As aerosol is drawn through the central channel 384 of the gasket 310, shown in FIG. 4, or as aerosol exits the capillary 18, shown in FIGS. 2 and 3, the aerosol is directed against the MAC insert 32, whereupon heat is exchanged such that the temperature of the aerosol is reduced. In some cases, the temperature can be reduced by 30° C. or more as compared to aerosols which pass through a mouth end insert, as described herein, but lacking the MAC insert 32. When the aerosol strikes the MAC insert 32, larger aerosol particles tend to break up to form several smaller particles before the aerosol flows through the one or more air passages 38 extending through the MAC insert 32. As shown in Table 1 below, use of a mouth end insert including a MAC insert as described herein provides an aerosol having a lower temperature, in degrees Celsius, as compared to aerosols which pass through a mouth end insert excluding the MAC insert.

TABLE 1

| Mouth End Insert | $1^{st}$ Puff (° C.) | $2^{nd}$ Puff (° C.) | 3rd Puff (° C.) | 4th Puff (° C.) | 5th Puff (° C.) | 6th Puff (° C.) | 7th Puff (° C.) | 8th Puff (° C.) | $9^{th}$ Puff (° C.) | $10^{th}$ Puff (° C.) | $11^{th}$ Puff (° C.) | Avg. (° C.) | Std. Dev. (° C.) |
|---|---|---|---|---|---|---|---|---|---|---|---|---|---|
| Without MAC insert | 90.8 | 92.1 | 93.6 | 95.6 | 91.5 | 87.0 | 94.2 | 94.0 | 90.5 | 90.9 | 86.6 | 91.5 | 2.8 |
| Embodiment of FIG. 7 | 70.0 | 73.4 | 73.0 | 70.5 | 74.2 | 72.5 | 73.0 | 72.8 | 70.5 | 69.2 | 67.6 | 71.5 | 2.1 |

TABLE 1-continued

| Mouth End Insert | 1st Puff (° C.) | 2nd Puff (° C.) | 3rd Puff (° C.) | 4th Puff (° C.) | 5th Puff (° C.) | 6th Puff (° C.) | 7th Puff (° C.) | 8th Puff (° C.) | 9th Puff (° C.) | 10th Puff (° C.) | 11th Puff (° C.) | Avg. (° C.) | Std. Dev. (° C.) |
|---|---|---|---|---|---|---|---|---|---|---|---|---|---|
| Embodiment of FIG. 8 | 60.6 | 66.8 | 68.9 | 69.5 | 68.5 | 69.1 | 69.5 | 71.8 | 70.5 | 71.8 | 74.9 | 69.3 | 3.6 |
| Embodiment of FIG. 9 | 57.2 | 70.0 | 65.8 | 65.2 | 64.4 | 67.6 | 71.7 | 71.7 | 67.0 | 66.4 | 74.5 | 67.4 | 4.6 |

It is believed that upon exiting the central channel 384 of the gasket 310 or the capillary 18, the aerosol comprises large particles of propylene glycol and water and relatively large, separate particles of nicotine droplets. The relatively large, nicotine droplets comprise a vapor phase component of the aerosol and are known to contribute undesirable sensory responses such as throat irritation and/or harshness when inhaled.

Not wishing to be bound by theory, upon striking the MAC insert 32 of the mouth end insert 20, it is believed that the aerosol undergoes a transformation whereby larger particles of the aerosol as previously described become smaller particulate phase constituents.

As a result of drawing the aerosol through the mouth end insert 20 including the MAC insert 32, it has been found that the aerosol of the electronic smoking article 60 tends to be lower in temperature, to have a particle size distribution that has shifted toward a range of smaller particle sizes. The reduced aerosol temperature is believed to improve mouth feel.

Optionally, the MAC insert 32 of the mouth end insert 20 may be porous such that it has the capacity to collect particles through adsorption and/or absorption. For example, the MAC insert 32 can be a foamed insert or a ceramic insert.

Referring to FIG. 12, the MAC insert disc 332 of the embodiments shown in FIG. 7 includes a plurality of vanes 335 that define minute air passages 38 therebetween. Preferably, the disc 332 is constructed from machine stamped sheet metal of approximately 0.5 mm thickness. There are about 25 vanes of the illustrated embodiment. The large number of vanes 335 and the small size of the passages 38 enhance aerosol-to-surface contact of the vanes, which enhances cooling (through heat transfer) of the aerosol.

Advantageously, this embodiment provides heat transfer through impaction at a central portion of the disc 332 and through splitting the flow into a large number of minute flowlettes which come into intimate contact with the vanes 335.

It is contemplated that the disc 332 and the bars 432 of the various embodiments may be established in a separate cylindrical piece 290.

When the word "about" is used in this specification in connection with a numerical value, it is intended that the associated numerical value include a tolerance of +10% around the stated numerical value. Moreover, when reference is made to percentages in this specification, it is intended that those percentages are based on weight, i.e., weight percentages. The expression "up to" includes amounts of zero to the expressed upper limit and all values therebetween. When ranges are specified, the range includes all values therebetween such as increments of 0.1%.

Moreover, when the words "generally" and "substantially" are used in connection with geometric shapes, it is intended that precision of the geometric shape is not required but that latitude for the shape is within the scope of the disclosure. When used with geometric terms, the words "generally" and "substantially" are intended to encompass not only features which meet the strict definitions but also features which fairly approximate the strict definitions.

It will now be apparent that a new, improved, and nonobvious electronic smoking article and mouth end insert has been described in this specification with sufficient particularity as to be understood by one of ordinary skill in the art. Moreover, it will be apparent to those skilled in the art that numerous modifications, variations, substitutions, and equivalents exist for features of the electronic smoking article and mouth end insert which do not materially depart from the spirit and scope of the invention. Accordingly, it is expressly intended that all such modifications, variations, substitutions, and equivalents which fall within the spirit and scope of the invention as defined by the appended claims shall be embraced by the appended claims.

We claim:

1. An electronic vaping device comprising:
   an outer tube extending in a longitudinal direction;
   a liquid aerosol formulation;
   a filamentary wick or a capillary configured to receive the liquid aerosol formulation;
   a heater in communication with the filamentary wick or the capillary, the heater configured to heat the liquid aerosol formulation to produce a volatilized aerosol formulation; and
   a mouth-end insert including,
      a downstream end wall having at least two diverging outlet passages extending therethrough, the downstream end wall being planar at a first end,
      a cylindrical side wall extending from the downstream end wall in the longitudinal direction, at least a portion of the cylindrical side wall configured to be received in the outer tube, the cylindrical side wall having an inner surface facing an interior of the electronic vaping device in a direction perpendicular to the longitudinal direction,
      a mechanical aerosol converter (MAC) portion upstream of the end wall including at least one air passage extending longitudinally therethrough, thereby, or both therethrough and thereby, the MAC portion being disc shaped and contacting at least a portion of the cylindrical side wall on the inner surface of the cylindrical side wall, the MAC portion being friction fit within the cylindrical side wall, and
      an internal cavity arranged between the downstream end wall and the MAC portion, the downstream end wall having an inner surface shaped such that the internal cavity has a domed shape adjacent the downstream end wall, the internal cavity in fluid communication with the at least one air passage and the at least two diverging outlet passages.

2. The electronic vaping device of claim 1, wherein the at least one air passage includes up to 40 air passages.

3. The electronic vaping device of claim 2, wherein the up to 40 air passages are disposed radially outward of a central portion of the MAC portion.

4. The electronic vaping device of claim 1, further comprising:
an inner tube within the outer tube, the heater being located in the inner tube; and
a reservoir in communication with the filamentary wick, wherein the reservoir is contained in an outer annulus between the outer tube and the inner tube.

5. The electronic vaping device of claim 1, wherein the MAC portion is porous and configured to retain particles of the volatilized aerosol formulation.

6. The electronic vaping device of claim 1, wherein the at least two diverging outlet passages are angled at 5 degrees to 60 degrees in relation to a longitudinal axis of the electronic vaping device.

7. The electronic vaping device of claim 1, wherein the at least one air passage has (a) a diameter or (b) a length and a width in a transverse direction ranging from 0.25 mm to 1.25 mm.

8. The electronic vaping device of claim 1, wherein the MAC portion is formed of a plastic or metal.

9. An electronic vaping device comprising:
an outer tube extending in a longitudinal direction;
a liquid aerosol formulation;
a filamentary wick or a capillary configured to receive the liquid aerosol formulation;
a heater in communication with the filamentary wick or the capillary, the heater configured to heat the liquid aerosol formulation to produce a volatized aerosol formulation; and
a mouth-end insert including,
a downstream end wall having at least one diverging outlet passage extending therethrough, the downstream end wall being planar at a first end,
a cylindrical side wall extending from the downstream end wall in the longitudinal direction, at least a portion of the cylindrical side wall configured to be received in the outer tube, the cylindrical side wall having an inner surface facing an interior of the electronic vaping device in a direction perpendicular to the longitudinal direction,
a mechanical aerosol converter (MAC) portion upstream of the end wall, including at least one air passage extending longitudinally therethrough, thereby or both therethrough and thereby, the MAC portion having a gear shape and contacting the cylindrical side wall on the inner surface of the cylindrical side wall, the gear shape including a plurality of trapezoidal shaped portions extending from the cylindrical side wall to an inner portion of the MAC portion, the MAC portion being friction fit within the cylindrical side wall, and
an internal cavity arranged between the downstream end wall and the MAC portion, the downstream end wall having an inner surface shaped such that the internal cavity has a dome shape adjacent the downstream end wall, the internal cavity in fluid communication with the at least one air passage and the at least one diverging outlet passage.

10. The electronic vaping device of claim 1, wherein
the electronic vaping device includes the filamentary wick,
the heater is a coil heater, and
the filamentary wick is configured to draw the liquid aerosol formulation via capillary action.

11. The electronic vaping device of claim 1, further comprising:
a reservoir, wherein
the electronic vaping device includes the capillary, the capillary being in fluid communication with the reservoir, and
the heater comprises the capillary.

12. The electronic vaping device of claim 11, wherein the reservoir is pressurized and includes a mechanically or electrically operated valve at an outlet of the reservoir.

13. The electronic vaping device of claim 11, wherein the reservoir is compressible such that the liquid aerosol formulation is manually pumped to the capillary.

14. The electronic vaping device of claim 1, wherein the MAC portion is flush with an upstream end of the mouth-end insert.

15. The electronic vaping device of claim 9, wherein the MAC portion is flush with an upstream end of the mouth-end insert.

16. The electronic vaping device of claim 1, wherein the internal cavity has a length ranging from 1.0 mm to 5.0 mm.

17. The electronic vaping device of claim 1, wherein the MAC portion has a thickness ranging from 0.25 mm to 1.25 mm.

18. The electronic vaping device of claim 1, wherein the mouth-end insert is configured to reduce a temperature of the volatilized aerosol formulation produced by the electronic vaping device by at least 10 degrees Celsius.

19. The electronic vaping device of claim 1, wherein
the electronic vaping device includes the capillary, the capillary being in fluid communication with a reservoir, and
the heater is arranged along at least a portion of the capillary.

* * * * *